United States Patent [19]

Jovanovics et al.

[11] 4,310,528
[45] Jan. 12, 1982

[54] PROCESS FOR THE PREPARATION OF BIS-INDOLE ALKALOIDS AND ACID-ADDITION SALTS THEREOF AND METHODS OF TREATING TUMORS WITH BIS-INDOLE ALKALOIDS

[75] Inventors: Karola Jovanovics; Sandor Görög, both of Budapest, Hungary

[73] Assignee: Richter Gedeon Vegyeszeti Gyar Rt., Budapest, Hungary

[21] Appl. No.: 138,340

[22] Filed: Apr. 8, 1980

Related U.S. Application Data

[63] Continuation-in-part of Ser. No. 61,353, Jul. 27, 1979.

[30] Foreign Application Priority Data

Apr. 23, 1979 [HU] Hungary ................................ RI 708

[51] Int. Cl.$^3$ ................... A61K 31/475; C07D 519/04
[52] U.S. Cl. ................................. 424/262; 260/244.4
[58] Field of Search ...................... 260/244.4; 424/262

[56] References Cited

U.S. PATENT DOCUMENTS

| | | | |
|---|---|---|---|
| 3,392,173 | 7/1968 | Hargrove | 260/244.4 |
| 3,899,493 | 8/1975 | Jovanovics et al. | 260/244.4 |
| 4,110,330 | 8/1978 | Barnett et al. | 260/244.4 |
| 4,189,432 | 2/1980 | Jovanovics et al. | 260/244.4 |

*Primary Examiner*—Donald G. Daus
*Assistant Examiner*—Diana G. Rivers
*Attorney, Agent, or Firm*—Karl F. Ross

[57] ABSTRACT

A process for the preparation of diindole-alkaloids, especially new compounds corresponding to vinblastine or leurosine, in which the N-methyl group is replaced by an N—CH$_2$—O—R group wherein R is lower alkyl, having antitumor properties. The starting materials are subjected to oxidation by chromic acid or an alkali metal dichromate at temperatures from $-90°$ C. to $-30°$ C. and preferably below $-45°$ C. where the new compounds are to be produced, a lower alkanol being present in this case.

7 Claims, 6 Drawing Figures

FIG. 2  RGH-4451 ¹H-NMR SPECTRUM

FIG. 3 RGH-4451 $^{13}$C-NMR SPECTRUM

FIG.4 RGH-4478 – INFRARED SPECTRUM

PROCESS FOR THE PREPARATION OF BIS-INDOLE ALKALOIDS AND ACID-ADDITION SALTS THEREOF AND METHODS OF TREATING TUMORS WITH BIS-INDOLE ALKALOIDS

CROSS REFERENCE TO RELATED APPLICATION

This application is a continuation-in-part of copending application Ser. No. 061,353 filed July 27, 1979.

The present invention relates to a process for the preparation of bis-indole-alkaloids and acid-addition salts thereof, as well as to new bis-indole-alkaloids. More particularly, the invention concerns the oxidation of the N-methyl group of vinblastine, leurosine or the acid-addition salts thereof by chromic acid ($CrO_3$) or a salt thereof. Oxidation of vinblastine or an acid-addition salt thereof yields the known N-desmethyl-vinblastine and vincristine (also called as N-desmethyl-N-formyl-vinblastine) and also new compounds of the formula Ia

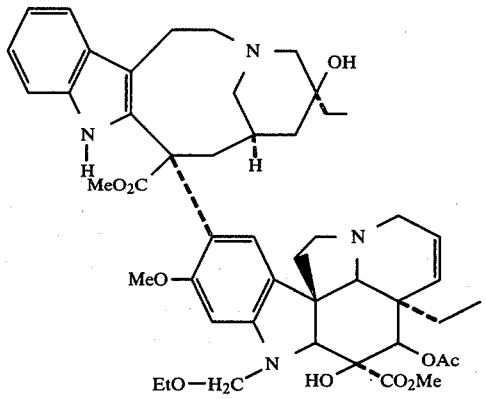

When leurosine or an acid-addition salt thereof is oxidized, in addition to the known N-desmethyl-leurosine and N-desmethyl-N-formyl-leurosine new compounds of the formula Ib are obtained.

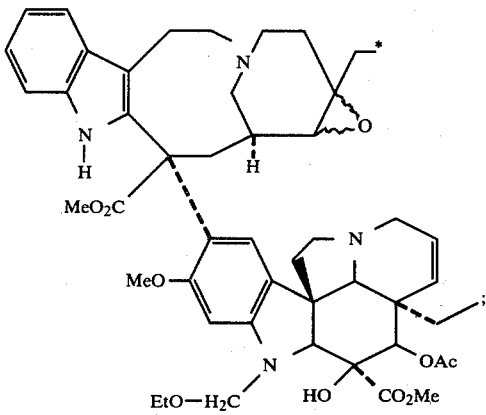

The new compounds contain an N—$CH_2$—OH-ethyl group in place of the N-methyl group of vinblastine and leurosine.

The starting compounds used in this process according to the invention are known in the art. Vinblastine and acid-addition salts thereof are for example described in U.S. Pat. No. 3,097,137, while leurosine is the subject of U.S. Pat. No. 3,370,057. Vinblastine is used as an antitumor agent also in clinical practice. The trade name of the composition containing vinblastine is Velbe. Also the antitumor activity of leurosine has been proved on animals but it cannot successfully be used in human therapy due to its unreasonably high toxicity on the hematopoietic organs (Rohn, R. et al: *Cancer Chemother. Reports*, 38, 53, 1963).

The preparation of vincristine is for example described in U.S. Pat. No. 3,205,220, in Belgian Pat. No. 819,663, in Hungarian Pat. Nos. 168,433 and 165,599 (corresponding to U.S. Pat. No. 3,899,493) and in German Pat. No. 2,614,863; and N-desmethyl-vinblastine can be prepared according to U.S. Pat. No. 3,354,163, Belgian Pat. No. 819,078 and Hungarian Pat. No. 165,599. N-desmethyl-N-formyl-leurosine and N-desmethyl-leurosine are disclosed in Hungarian Pat. No. 165,986 (corresponding to British Pat. No. 1,412,932). N-desmethyl derivatives have no notable antitumor activity. N-formyl derivatives are first of all capable of controlling acute leukemia and various lymphomic diseases; while vincristine is used for the treatment of psoriasis (see U.S. Pat. No. 3,749,784).

Since the use of diindole-alkaloids is accompanied by toxic side effects—for instance the administration of vincristine induces paralytic symptoms due to neurotoxicity—a considerable effort has been made to prepare new derivatives having the same or similar activity without or with less undesired toxic effects. On the other hand, diindole-alkaloids, which cannot be directly utilized for medical purposes are often converted into pharmacologically utilizable alkaloids.

For example according to the process disclosed in Hungarian Pat. No. 165,986 leurosine is converted into the effective, non-toxic N-desmethyl-N-formyl-leurosine; or according to Hungarian Pat. No. 165,599 vinblastine is transformed into the more effective N-formyl derivative, i.e. vincristine. According to these processes the starting compound is oxidized with chromium trioxide in a mixture of glacial acetic acid, acetone and acetic anhydride at a temperature between $-90°$ C. and $-30°$ C., whereupon the reaction mixture is neutralized and from the mixture obtained containing N-desmethyl- and N-formyl-leurosine the components are separated, or, if desired, N-desmethyl derivative is converted into the corresponding N-formyl derivative by a suitable formylating agent.

DESCRIPTION OF THE INVENTION

The purpose of this invention is to provide a new oxidation procedure and new oxidative derivatives.

It has surprisingly been found that if in the above process acetone is replaced by a water-immiscible organic solvent, in which alkaloids are readily soluble, preferably by a chlorinated hydrocarbon, and a small amount of a ethanol, oxidation affords also new compounds. More specifically, oxidation of vinblastine results, in addition to the known compounds, in the formation of new derivatives such as "RGH-4451" (formula Ia); and in an analogous way by oxidation of leurosine, other new compounds such as "RGH-4478" (formula Ib) are also obtained. The new compounds contain an N—$CH_2$—O-ethyl group in place of the N-methyl group of the starting compounds in the vindoline moiety.

In addition to the new compound, by the above oxidation the corresponding N-desmethyl- and N-desmethyl-N-formyl derivatives are also obtained. It should be noted that the presence of the ethanol is not essential with respect to the formation of the known compounds.

On the other hand the new compounds are only obtained if the ethanol is present. It is also preferable that the temperature of the reaction be no greater than $-45°$ C. Where the temperature exceeds $-45°$ C., it becomes more difficult to isolate the product.

It has further been found that the new "RGH" compounds can be converted into the corresponding known N-desmethyl derivatives by an acid treatment, and the latter compounds can thereafter by converted into the corresponding N-desmethyl-N-formyl derivatives by known methods per se.

The use of a different solvent system also has a technological advantage; due to the two-phase reaction system the oxidation and the subsequent neutralization are less exothermic, easy to control and the danger of decomposition of the heat-unstable diindole compounds is considerably decreased. This technological advantage has nothing to do with the presence of the ethanol.

The new compounds prepared according to the invention had been subjected to extensive comparative pharmacological tests, and it has been concluded that from a pharmacological point of view RGH-4451 is the most advantageous among the compounds obtained.

The acute toxicity of RGH-4451 was tested on mice. The $LD_{50}$-value of this new compound amounted to 70 mg/kg i.p., which is 17-fold of that of vincristine, about 10-times higher than that of vinblastine and 2.5-times higher than that of N-desmethyl-N-formyl-leurosine.

The lethal dose killed the animals on the 2nd to 5th day. The death was not accompanied by paralytic symptoms and, in contrast with the results obtained with vincrinstine, the surviving animals were not crippled even temporarily.

The inhibition of tumor growth was initially studied in a tissue culture. A 20 mg/ml solution of RGH-4451 in Fischer medium was prepared and subsequently diluted to the desired concentration. The number of cells in the P 388 cultures was determined 24 and 48 hours after treatment.

In a concentration of $10^{-1}$ μg/ml the RGH-4451 considerably inhibited the growth of P 388 tumor cells. The inhibition was 43% after 24 hours and 89% after 48 hours. In in vitro tests the compound was 100-times less toxic than vincristine and 4-times less toxic than N-desmethyl-N-formyl-leurosine.

The inhibition of tumor growth was examined also on transplanted rodent tumors.

Effect on P 388 leukemia tumors of mice $10^6$ P 388 leukemia cells were transplanted into $BDF_1$ hybrid mice intraperitoneally. Administration of RGH-4451 was started the day following the transplantation. The results obtained are summarized in the following table:

| DOSE MG/KG I.P. | NUMBER OF TREATMENTS | FREQUENCY | MEAN DURATION OF LIFE EXPRESSED IN DAYS TREATED | MEAN DURATION OF LIFE EXPRESSED IN DAYS CONTROL | EXPRESSED IN % OF TREATED CONTROL |
|---|---|---|---|---|---|
| 3.2 | 9 | every day | 22.3 | 12.3 | 181 |
| 5.0 | 9 | every day | 21.5 | 13.2 | 163 |
| 6.4 | 9 | every day | 20.5 | 12.3 | 166 |
| 10 | 5 | every second day | 21.8 | 10.5 | 208 |
| 20 | 6 | every day | 8.5 | 13.2 | 64 |
| 20 | 1 | — | 19.4 | 10.5 | 185 |

From the table it can be seen that the duration of life of the tumorous animals has considerably been prolonged by administration of 3.2 to 6.4 mg/kg doses every day. A 10 mg/kg dose administered every second day had an even more favorable effect. It can also be seen that a single 20 mg/1g dose is also effective, but this large dose cannot be administered every day due to its toxicity. A similar effect was achieved with 0.1 to 0.3 mg/kg/day doses of vincristine, 1.0 to 4.0 mg/kg/day doses of N-desmethyl-N-formyl-leurosine and 0.1 to 0.4 mg/kg/day doses of vinblastine.

Effect on Ehrlich ascites carcinoma

Transplantation was carried out into outbred Swiss mice at a level of $5 \times 10^6$ ascites tumor cells. Administration of RGH-4451 was started 24 hours after transplantation. The results obtained are shown in the following table:

| DOSE MG/KG I.P. | NUMBER OF TREATMENTS | FREQUENCY | MEAN DURATION OF LIFE EXPRESSED IN DAYS TREATED | MEAN DURATION OF LIFE EXPRESSED IN DAYS CONTROL | EXPRESSED IN % OF TREATED/CONTROL |
|---|---|---|---|---|---|
| 1.0 | 9 | every day | 54.2 | 15.4 | 341 |
| 2.0 | 9 | every day | 43.0 | 16.4 | 261 |
| 4.0 | 9 | every day | 36.4 | 16.4 | 222 |
| 6.0 | 9 | every day | 48.2 | 15.9 | 303 |

From the above results it can be clearly seen that the effect of doses between 1.0 and 6.0 mg/kg is significant.

Effect on NK/Ly ascites lymphoma

Tests were carried out analogously with the Ehrlich ascites test.

The results obtained are listed in the following table:

| DOSE | | | MEAN DURATION OF LIFE | | | ON THE 65TH DAY | |
|---|---|---|---|---|---|---|---|
| | | | EXPRESSED IN DAYS | | EXPRESSED IN % OF | | TUMOR- |
| MG/KG I.P. | NUMBER OF TREATMENTS | FREQUENCY | TREATED | CONTROL | TREATED*/CONTROL | ALIVE | FREE |
| 2.0 | 9 | every day | 64.1 | 16.4 | 392 | 9/10 | 6/10 |
| 4.0 | 9 | every day | 62.9 | 16.4 | 384 | 8/10 | 7/10 |
| 6.0 | 9 | every day | 65.8 | 16.7 | 394 | 8/10 | 4/10 |
| 20 | 1 | — | 65.5 | 16.7 | 392 | 8/10 | 3/10 |

*A life span of four-times the mean duration of life of the control group would be 400%.

From the results it can be seen that the 2 to 6 mg/kg doses administered once a day have a remarkable antitumor effect, a great part of the treated animals is tumor-free on the 65th day. A similar result is obtained when a single large dose is administered.

0.05 to 0.25 mg/kg daily doses of vincristine and 1 to 4 mg/kg daily doses of N-desmethyl-N-formyl-leurosine have a similar effect. In this case, however, the adiminstration of a large single dose did not increase the duration of life.

Effect on S 180 sc. carcinoma

S 180 sc. tumor tissues were transplanted into Swiss mice subcutaneously. Treatment was started 24 hours after transplantation. RGH-4451 was administered once a day in a dose of 2, 4, 8 and 16 mg/kg, respectively intraperitoneally. The tumor growth inhibition was evaluated on the 11th day on the basis of the weight of tumors. The change of the weight of spleen was also monitored.

The tumor-growth inhibition observed upon administration of RGH-4451 was about the same as in the case of known diindole-alkaloids (34 to 56% depending on the dose) but the daily doses of the new compound could be higher and there was no substantial decrease in the weight of spleen even at as high doses as 16 mg/kg.

Effect of Guerin sc. carcinoma

Tumor was transplanted into Wistar rats subcutaneously. Administration of RGH-4451 was started on the day following the transplantation and the compound was administered six subsequent days intraperitoneally. The inhibition of tumor growth was evaluated on the 22nd day. The results obtained are listed in the following table:

| DOSE MG/KG I.P. | WEIGHT OF TUMOR | | IN- HIBITION | MORTALITY UNTIL THE 22ND DAY/NUMBR OF ANIMALS |
|---|---|---|---|---|
| | TREAT- ED | CON- TROL | | |
| 2.0 | 10.7 | 18.9 | 43 | 0/6 |
| 6.0 | 8.69 | 44.9 | 81 | 0/6 |
| 10.0 | 14.64 | 44.9 | 68 | 0/6 |
| 14.0 | — | — | — | 5/6 |

2 to 10 mg/kg i.p. doses of RGH-4451 strongly inhibited the growth of Guerin carcinoma.

From the tests described hereinabove it can be concluded that 1.0 to 10.0 mg/kg daily doses or 20 mg/kg single doses of RGH-4451 have a significant tumor-growth inhibition effect and prolong the duration of life.

By contrast with vincristine, paralytic symptoms are entirely lacking even when sublethal doses are administered. The therapeutic width of the tested new compound is greater than that of vincristine and N-desmethyl-N-formyl-leurosine as shown in the following table:

| | MTD/MIN EFF. |
|---|---|
| RGH-4451 | 10 |
| Vincristine | 6 |
| N-desmethyl-N-formyl-leurosine | 4 |

In human therapy for infusion or intravenous administration 0.5 to 1.0 mg/kg daily doses are advantageously used.

Figure 1:
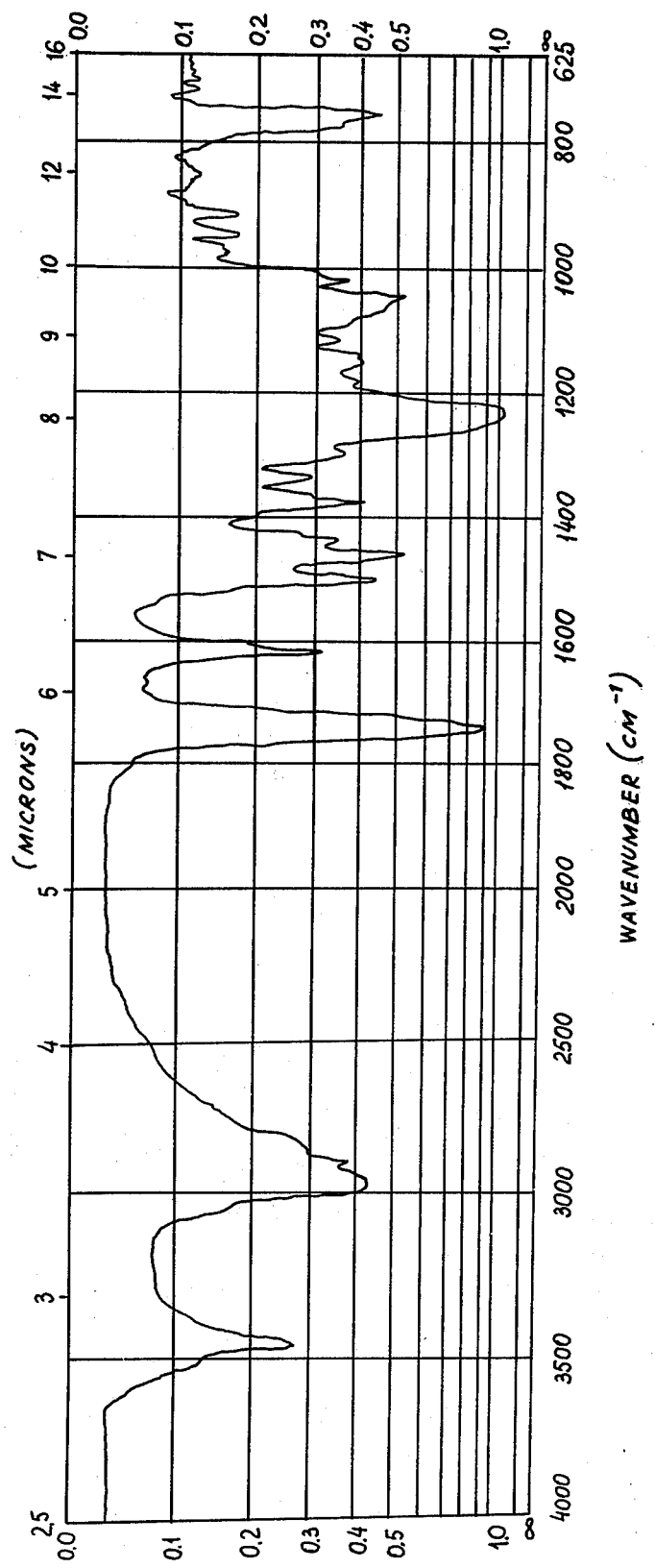
FIG. 1 is an infrared spectrum of one of the compounds of the present invention.
Figure 2:
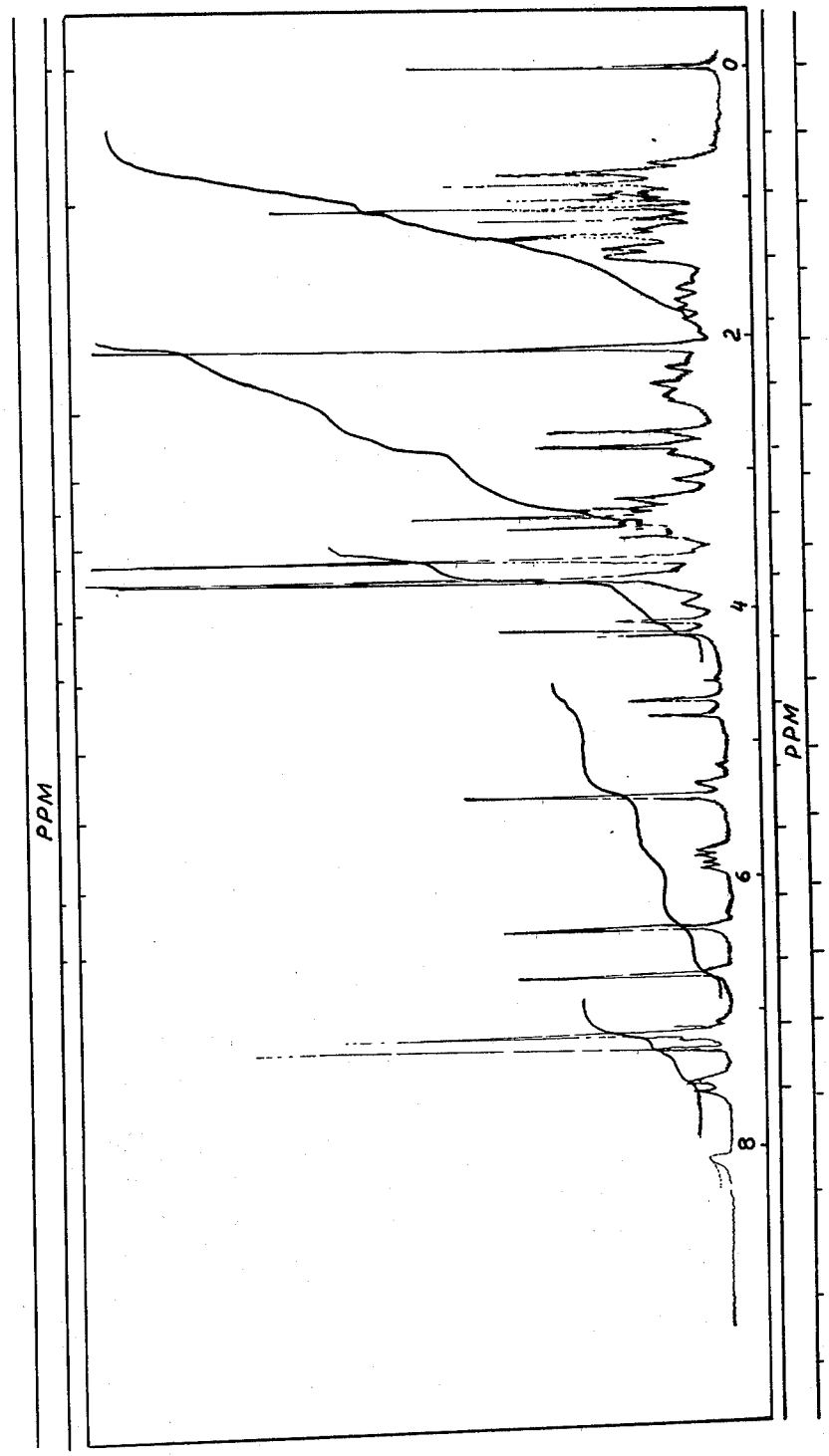
FIG. 2 is a nuclear magnetic resonance spectrum thereof.
Figure 3:
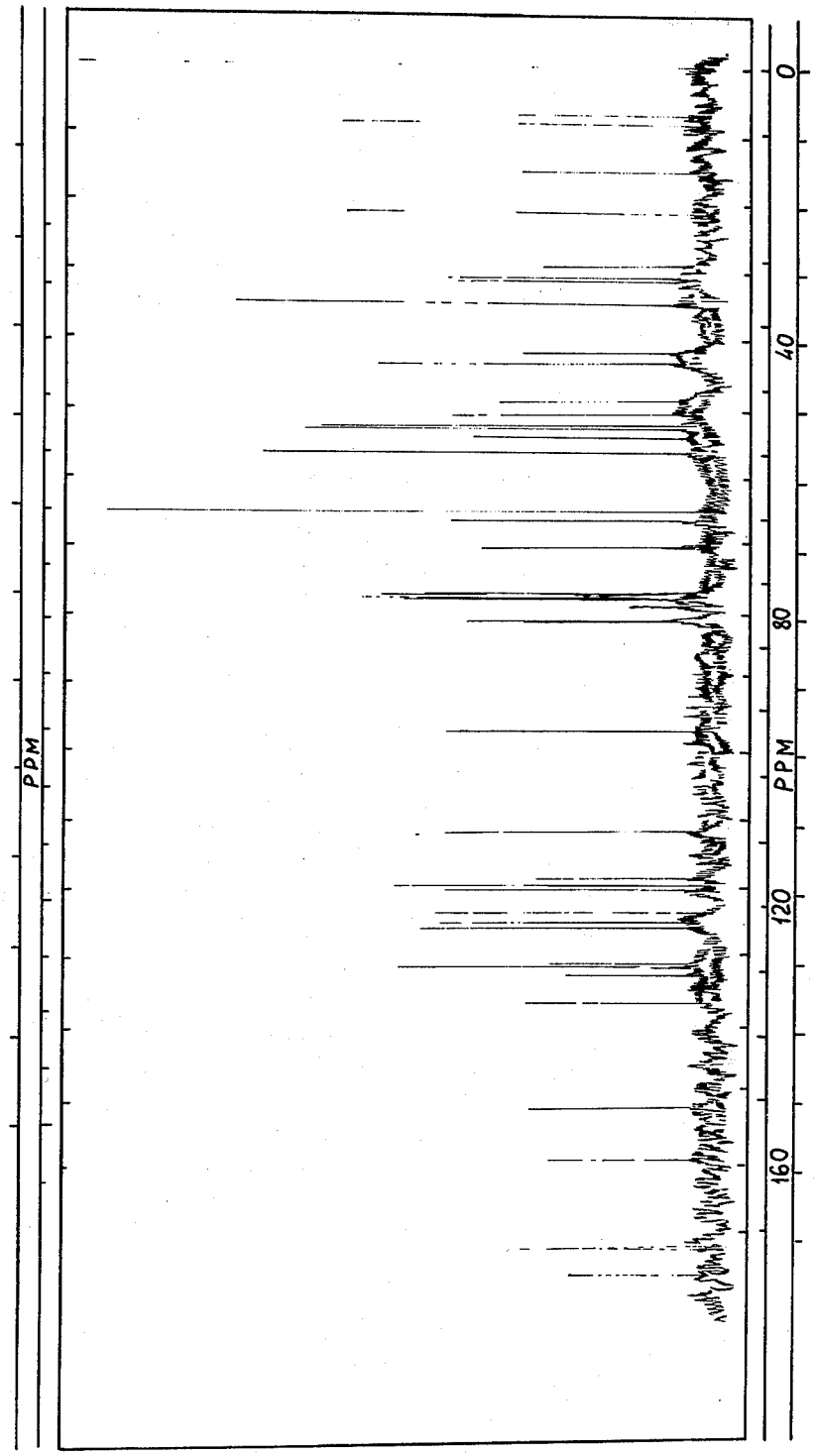
FIG. 3 is another nuclear magnetic reasonance spectrum thereof.
Figure 4:
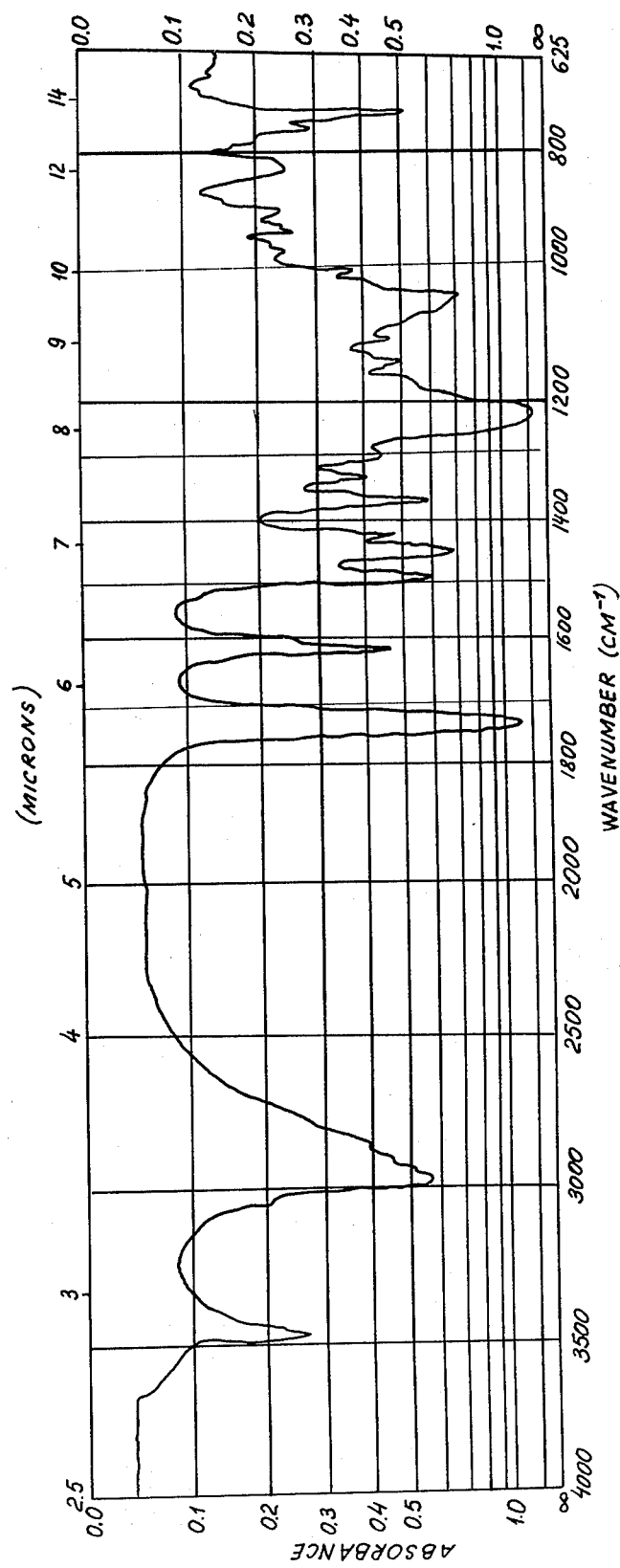
FIG. 4 is an infrared spectrum of another compound of the invention.
Figure 5:
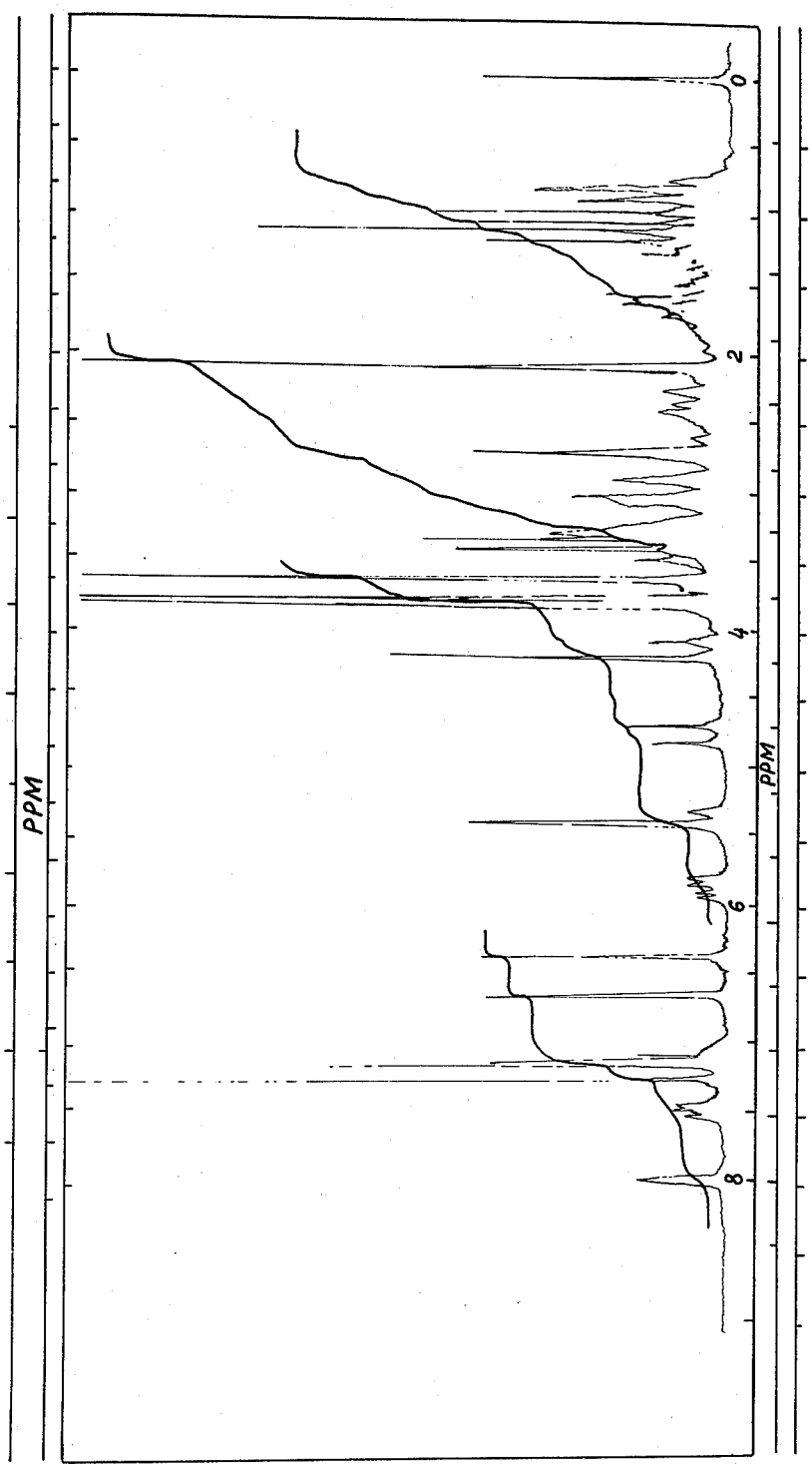
FIG. 5 is a nuclear magnetic resonance spectrum thereof.
Figure 6:
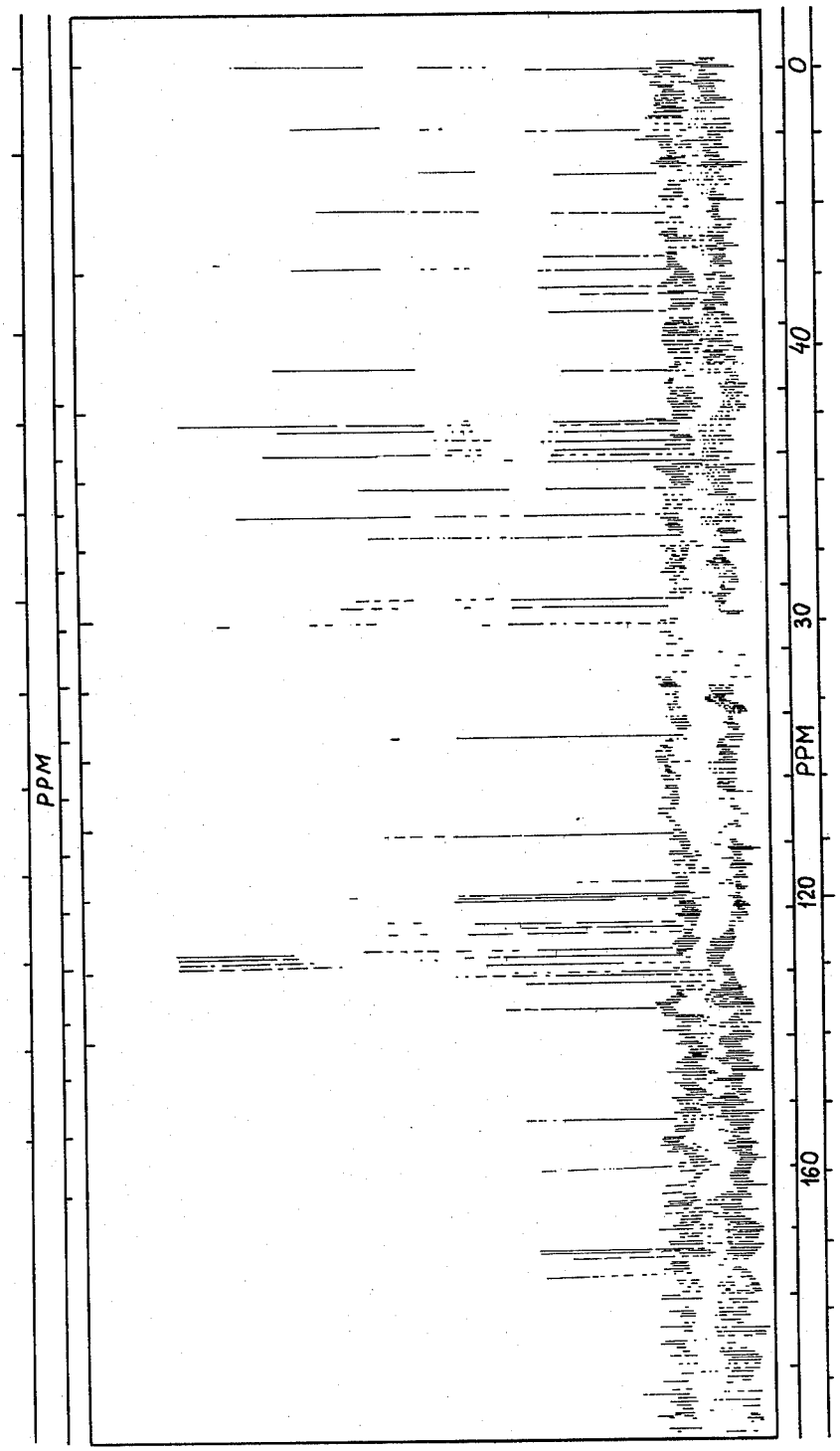
FIG. 6 is another nuclear magnetic resonance spectrum.

The invention relates to a process for the oxidation of vinblastine and leurosine or acid-addition salts thereof by chromic acid or by an alkali metal dichromate in the presence of an organic solvent, and acetic anhydride at a low temperature, optionally in the presence of glacial acetic acid and optionally to the formylation of the mixture obtained. The process is characterized in carrying out the oxidation at a temperature of $-30°$ C. to $-90°$ C., preferably at a temperature not exceeding $-45°$ C., in a medium containing as an organic solvent a water-immiscible organic solvent, preferably a chlorinated hydrocarbon and optionally ethanol preferably in a concentration lower than 10% related to the volume of solvent, in the presence of acetic anhydride, optionally in the presence of glacial acetic acid, and adjusting the pH of the reaction mixture to 8 to 10, and (a) from the organic phase isolating the components of the product mixture obtained, i.e.

if vinblastine or an acid-addition salt thereof is oxidized N-desmethyl-vinblastine, vincristine and optionally the compound designated "RGH-4451", which has the following characteristics:

melts at 235° C. to 238° C., has a specific rotary power of $[\alpha]_D^{25} = +30.5°$ (c=1, chloroform), has an infrared spectrum as illustrated in FIG. 1, has a $^1$H—NMR spectrum illustrated in FIG. 2, has a $^{13}$C—NMR spectrum illustrated in FIG. 3, which indicates that the structure of the molecule differs from vinblastine in containing an N—CH- $_2$—O—C$_2$H$_5$ group in place of an N-methyl group, in the vindoline moiety of the molecule and has a molecular weight of 854.499 corresponding to the formula of C$_{48}$H$_{62}$N$_4$O$_{10}$; or if leurosine or an acid-addition salt thereof is oxidized N-desmethyl-leurosine, N-desmethyl-N-formyl-leurosine and optionally the new compounds designated "RGH-4478" which has the following characteristics:

melts at 180° C. to 182° C., has a specific rotary power of $[\alpha]_D^{25} = +59.25°$ (c=1, chloroform), has an infrared spectrum illustrated in FIG. 4, has a $^1$H-NMR spectrum illustrated in FIG. 5 and has a $^{13}$C-NMR spectrum illustrated in FIG. 6, which indicates that the structure of this molecule differs from leurosine in containing an N—CH$_2$—O—C$_2$H$_5$ group in place of the N-methyl group in the vindoline moiety of the molecule, and has a molecular weight of 852 corresponding to the formula of C$_{48}$H$_{60}$N$_4$O$_{10}$ and, if desired, converting the products obtained into the acid-addition salts thereof; or (b) optionally hydrolyzing the product mixture present in the organic phase, if desired formylating the mixture of N-desmethyl and N-desmethyl-N-formyl derivative obtained in a manner known per se, and isolating the N-desmethyl-N-formyl derivative obtained, i.e. vincristine if vinblastine or an acid-addition salt thereof is oxidized, or N-desmethyl-N-formyl-leurosine if leurosine or an acid-addition salt thereof is oxidized, in a known manner, and if desired converting the product obtained into an acid-addition salt thereof.

In the process according to the invention as a starting material, technical or pharmacopeal vinblastine or a salt thereof, and leurosine or a salt thereof, respectively can be used. If an alkaloid of technical quality is employed, the product obtained can be purified for example, by chromatographic methods. If the starting material is of pharmacopeal quality, the product is directly suitable for therapeutical application. As an oxidazing agent chromic acid (CrO$_3$) or an alkali metal dichromate can be used.

Oxidation is carried out in the presence of acetic anhydride, optionally in the presence of acetic acid, and of a water-immiscible organic solvent in which the alkaloids are readily soluble. Typical representatives of such solvents are benzene, chlorinated hydrocarbons, preferably chloroform or methylene chloride.

Optionally, i.e. if also "RGH"-compounds are to be prepared oxidation is carried out in the presence of ethanol. The ethanol is used in an amount of less than 10% related to the volume of the organic solvent, preferably in an amount of 0.1 to 3.0%.

The temperature of oxidation is between −30° C. and +90° C. N-desmethyl and N-desmethyl-N-formyl derivatives are always obtained under these conditions. If the reaction is carried out at a temperature not exceeding −45° C. also "RGH"-compounds can be easily isolated. If the reaction is performed over −45° C., it becomes more difficult to isolate the "RGH"-compounds.

When the oxidation is completed, the pH-value of the reaction mixture is adjusted to 8 to 10 taking care that the temperature does not exceed 50° C., and keeping the pH of the aqueous phase at or higher than 8.

The phases are then allowed to separate, and the alkaloids are isolated from the organic phase.

Following the reaction variant (a) the RGH-compound can also be isolated. In this case the alkaloid mixture obtained by evaporating the organic phase comprising the N-desmethyl derivative, N-desmethyl-N-formyl derivative and the "RGH"-compound is separated to its components by chromatography. Chromatography is performed on a column filled with partly deactivated alumina, carrying out the elution with various mixtures of benzene and a chlorinated hydrocabon. The identification of the alkaloids present in the various fractions is effected by thin-layer chromatography, the fractions containing the same alkaloids are combined and the alkaloids are isolated for example by evaporation. The alkaloids obtained, if desired, are purified and if desired are converted into pharmaceutically acceptable acid-addition salts, preferably sulfate salts thereof.

If desired, the N-desmethyl derivative is formylated. As the formylating agent a mixture of formic acid and acetic anhydride is preferably used.

If the process variant (b) is followed, the RGH-compound is not isolated, instead it can be converted into a corresponding N-desmethyl derivative by dilute aqueous acid, for instance a 0.5 to 5% aqueous sulphuric acid solution, hydrochloric acid solution or acetic acid.

The new compounds and/or acid-addition salts thereof can be transformed into pharmaceutical compositions, which are preferably administered parenterally.

The active ingredient is lyophilized, processed into dry ampoules, which are admixed with the contents of solvent ampoules containing the conventional additives, preferably immediately prior to administration.

In the solvent ampoules distilled water or a physiological sodium chloride solution is preferably used as a carrier, optionally together with a preserving agent (for example benzyl alcohol), antioxidant, milk sugar or buffers.

Administration is carried out in the form of infusion, preferably in a physiological saline solution.

The composition can contain also other pharmaceutically active compounds, for instance adjuvants (analgesics, cardiac restoratives), or other known cytostatics.

The present invention is further illustrated by the following non-limiting Examples.

EXAMPLE 1

5 g (5.5 mmoles) of vinblastine sulfate are dissolved in a mixture of 1.2 liters of a 1% solution of ethanol in chloroform and 250 ml of acetic acid. The solution obtained is cooled to −55° C. and a solution of 2.48 g (24.48 mmoles) of chromium trioxide in 930 ml of acetic anhydride at −55° C. is added. The reaction mixture is stirred for 40 minutes, whereupon the pH is adjusted to 9 to 10 with a concentrated aqueous ammonium hydroxide solution having a temperature of −45° C. to −50° C. Thereafter 5 liters of water are added to the two-phase reaction mixture and after a five-minute stirring the phases are allowed to separate. The chloroform phase is put aside and the aqueous phase is extracted with 0.5 liter of chloroform. The chloroform phases are combined and treated with two 2.5-liter portions of a 1% aqueous ammonium hydroxide solution. The phases are reseparated, and the chloroform phase is dried over sodium sulphate, filtered and the filtrate is evaporated to dryness under reduced pressure.

4.0 g of a mixture of vinblastine derivatives are obtained, which can be separated to the corresponding components by following the method described hereinbelow:

The product obtained (4.0 g) is dissolved in 24 ml of a 2:1 mixture of benzene and chloroform. The solution is then passed through a chromatographic column filled with 200 g of alumina having an activity grade of III, which has previously been wetted with a 2:1 mixture of benzene and chloroform. The alkaloids are eluted by using the following eluants in the given order:

1.2 liters of a 2:1 mixture of benzene and chloroform,
1.5 liters of a 1:1 mixture of benzene and chloroform,
0.9 liter of a 1:2 mixture of benzene and chloroform.

The various fractions obtained are examined by thin-layer chromatography (t.l.c.).

(a) Processing of the fraction obtained by elution with a 2:1 mixture of benzene and chloroform The first 400-ml fraction of the eluate is alkaloid-free, the further eluates obtained with a 2:1 mixture of benzene and chloroform contain a new compound. By combining and evaporating the alkaloid-containing fractions 1.88 g of a crude new compound are obtained. The compound is designated by "RGH-4451".

One or more recrystallizations of the crude product from a double amount of ethanol yields 1.30 g of a crystalline, chromatographically uniform RGH-4451 product, having a melting point of 235° C. to 238° C. (decomposition, after recrystallization from ethanol twice). $[\alpha]_D^{25} = +30.5°$ (c=1, chloroform). $R_f=0.62$ (adsorbent: silica gel; eluting mixture: 100:5:5:5 mixture of diethyl ether, ethanol, benzene and diethyl amine). Mass spectrum: According to the mass spectrum the molecular weight of the compound amounts to 854.449, which corresponds to the formula $C_{48}H_{62}N_4O_{10}$. The mass number of this molecule is greater than that of vinblastine by 44, by a $C_2H_4O$ unit. On the basis of fragmentation studies it could be unambiguously concluded that said unit is linked to the vindoline part of the molecule.

The $^1$H-NMR spectrum is shown in FIG. 2. From this spectrum the N-methyl singulette present at 2.73 ppm in the spectrum of vinblastine is lacking. On the other hand at 4.48 ppm the multiplette peak of the methylene of the group $N-CH_2-O$ can be seen, while the methyl triplette and methylene quartette of the group $O-C_2H_5$ appear at 1.05 and 3.35 ppm, respectively.

The $^{13}$C-NMR spectrum is shown in FIG. 3. The presence of the group $N-CH_2O$ is verified by the peak at 64.42 ppm (which has a triplette multiplicity in the off-resonancy spectrum).

On the basis of the above analysis a $CH_2-O-C_2H_5$ group is present in the molecule.

The IR spectrum of the compound can be seen in FIG. 1, where the characteristic group frequencies are as follows:

3470 cm$^{-1}$: OH valence
2970-2830 cm$^{-1}$: OH valence vibrations
1737 and 1230 cm$^{-1}$: acetyl groups
1612 cm$^{-1}$: C=C bond
1595 cm$^{-1}$: aromatic skeleton
742 cm$^{-1}$: 4 A —H next to each other.

The characteristic new bands of RGH-4451 having a low intensity appear at 995, 1170 and 1360 cm$^{-1}$.

It can also be seen that the low-frequency bands at 1090 cm$^{-1}$ and 700 cm$^{-1}$ characteristic of vinblastine disappear.

(b) Processing of the fraction obtained by elution with 1:1 mixture of benzene and chloroform The first 1000-1200 ml fraction of the eluate obtained when eluting with 1.5 liters of a 1:1 mixture of benzene and chloroform is a so-called mixed fraction consisting of the new compound called RGH-4451 and N-desmethyl-vinblastine, while the remaining 300-500 ml fraction contains N-desmethyl-vinblastine.

The mixed fraction is evaporated to give 0.57 g of a mixed solid, which is converted into N-desmethyl-vinblastine by the following technique: The evaporation residue is dissolved in 10 ml of benzene, the benzene solution is extracted with three 15 ml portions of a 2% aqueous hydrochloric acid solution, the phases are separated, whereupon the pH of the aqueous phase is adjusted to 9 with a concentrated aqueous ammonium hydroxide solution. The obtained alkaline solution is extracted with three 10 ml portions of chloroform, and the chloroform extract is evaporated. 0.56 g of N-desmethyl-vinblastine are obtained.

By evaporating the N-desmethyl-vinblastine fractions 0.08 g of N-desmethyl-vinblastine are obtained, which is combined with N-desmethyl-vinblastine obtained from the mixed fraction. N-desmethyl-vinblastine is converted into vincristine as described in Hungarian Pat. No. 165,599. Yield: 0.63 g of vincristine. Melting point: 218° C. to 220° C.

(c) Processing of the fraction obtained by elution with a 1:2 mixture of benzene and chloroform From the fraction obtained by elution with 0.9 liter of a 1:2 mixture of benzene and chloroform, vincristine can be isolated by evaporation. Yield: 1.22 g of vincristine. Melting point: 220° C.

EXAMPLE 2

5 g (5.5 mmoles) of vinblastine sulfate are dissolved in a mixture of 1.2 liters of a 1% solution of ethanol in chloroform and 250 ml of acetic acid. The solution obtained is cooled to −55° C. and a solution of 2.48 g (24.48 mmoles) of chromium trioxide in 930 ml of acetic anhydride of −55° C. is added. The reaction mixture is stirred for 40 minutes, whereupon the pH is adjusted to 9 to 10 with a concentrated aqueous ammonium hydroxide solution cooled to −45° C. to −55° C. Thereafter 5 liters of water are added to the two-phase reaction mixture and after a five-minute stirring the phases are allowed to separate. The chloroform phase is put aside and the aqueous phase is extracted with 0.5 liter of chloroform. The chloroform phases are combined and treated with two 2.5 liter portions of a 1% aqueous ammonium hydroxide solution. The phases are reseparated, and the chloroform phase is extracted with three 0.3 liter portions of an aqueous sulfuric acid solution, whereupon the pH of the extract is adjusted to 9 with a concentrated aqueous ammonium hydroxide solution. The alkaline extract is extracted with three 0.2 liter portions of chloroform. Evaporation of the extract affords an evaporation residue consisting of N-desmethyl-vinblastine and vincristine, which is converted to vincristine by formylation carried out as described in Hungarian Pat. No. 165,599. Treating with a solution of sulfuric acid in ethanol, the product obtained can be converted into vincristine sulfate. Yield: 3.6 g of vincristine sulfate.

EXAMPLE 3

5 g (5.5 mmoles) of vinblastine sulfate are dissolved in a mixture of 1.2 liters of a 1% solution of ethanol in chloroform and 250 ml of acetic acid. The solution obtained is cooled to −55° C. and a solution of 2.48 g (24.48 mmoles) of chromium trioxide in 930 ml of acetic anhydride of −55° C. is added. The reaction mixture is stirred for 40 minutes, whereupon it is poured into a mixture of 6 liters of water and 4 liters of a concentrated aqueous ammonium hydroxide solution cooled to +2° C. to +5° C. The reaction mixture is stirred for 5 minutes at a temperature below 20° C., ensuring that the pH value of the aqueous phase remains at least 8. The phases are then separated, the aqueous phase is extracted with 0.5 liter of chloroform and the extract is combined with the chloroform phase. The chloroform solution is extracted with two 2.5 liter portions of a 1% aqueous ammonium hydroxide solution, the phases are separated and the chloroform phase is dried. It is then (a) either evaporated according to Example 1, followed by separating the diindole-alkaloid mixture obtained weighing 4 g into its components, or (b) is converted into vincristine by an acid treatment and a subsequent formylation as described in Example 2.

If the (a) reaction route is followed the yield is identical with that obtained in Example 1, while the (b) reaction route affords the same yield as Example 2.

EXAMPLE 4

5 g (5.5 mmoles) of vinblastine sulfate are dissolved in a mixture of 1.2 liters of a 0.5% solution of ethanol in methylene chloride and 250 ml of acetic acid. The solution obtained is cooled to −55° C. and a solution of 2.48 g (24.48 mmoles) of chromium trioxide in 930 ml of acetic anhydride of −55° C. is added. The reaction mixture is stirred for 40 minutes, whereupon the pH is adjusted to 9 to 10 with a concentrated aqueous ammonium hydroxide solution cooled to −45° C. to −50° C. Thereafter 5 liters of water are added to the two-phase reaction mixture and after a five-minute stirring the phases are allowed to separate. The methylene chloride phase is put aside and the aqueous phase is extracted with 0.5 liter of methylene chloride. The methylene chloride phases are combined and treated with two 2.5 liter portions of a 1% aqueous ammonium hydroxide solution. The phases are reseparated, the methylene chloride phase is dried with sodium sulfate, filtered, whereupon the filtrate is evaporated to dryness under reduced pressure. Yield: 3.5 g of a mixture of diindole-alkaloids, which is separated into its components following the method described in Example 1.

The physical characteristics of RGH-4451 and vincristine, respectively are identical with the corresponding characteristics of the products of Example 1.

EXAMPLE 5

5 g of leurosine sulfate are dissolved in a mixture of 1.2 liters of a 1% solution of ethanol in chloroform and 250 ml of acetic acid. The solution obtained is cooled to −55° C. and a solution of 2.48 g (24.48 mmoles) of chromium trioxide in 930 ml of acetic anhydride of −55° C. is added. The reaction mixture is stirred for 40 minutes, whereupon the pH is adjusted to 9 to 10 with a concentrated aqueous ammonium hydroxide solution having a temperature of −45° C. to −50° C. Thereafter 5 liters of water are added to the two-phase reaction mixture and after a five-minute stirring the phases are allowed to separate. The chloroform phase is put aside and the aqueous phase is extracted with 0.5 liter of chloroform. The chloroform phases are combined and extracted with two 2.5 liter portions of a 1% aqueous ammonium hydroxide solution. The phases are reseparated, the chloroform phase is dried with sodium sulfate, filtered, whereupon the filtrate is evaporated to dryness under reduced pressure. Yield: 4.5 g of a mixture of leurosine derivatives, which is separated to the corresponding components by following the method described hereinbelow:

The product obtained (4.5 g) is dissolved in 27 ml of a 3:1 mixture of benzene and chloroform, and the solution is chromatographed on a column filled with alumina having an activity grade of III and treated with a 3:1 mixture of benzene and chloroform. The alkaloids are eluted with the following eluants in the given order:

3.5 liters of a 3:1 mixture of benzene and chloroform,
1 liter of a 2:1 mixture of benzene and chloroform,
2.5 liters of a 1:2 mixture of benzene and chloroform.
250 ml fractions are collected and the alkaloids contained therein are examined by thin-layer chromatography (t.l.c.).

The 1st to 6th fractions (1.5 liters) are alkaloid-free, the 7th to 14th fractions (3:1 mixture of benzene and chloroform) and the 15th to 17th fractions (2:1 mixture of benzene and chloroform) contain the new compound identified RGH-4478. The 18th fraction obtained with a 2:1 mixture of benzene and chloroform and the 19th to 23rd fractions obtained with a 1:2 mixture of benzene and chloroform contain N-desmethyl-leurosine, while the 24th to 28th fractions obtained by elution with a 1:2 mixture of benzene and chloroform contain N-desmethyl-N-formyl-leurosine.

The eluate fractions are processed as follows:

(a) The 7th to 17th fractions are combined and evaporated. 2.13 g of crude RGH-4478 are obtained, which is purified by crystallization from 5 ml of ethanol at 5° C. If desired, the product is dissolved in chloroform, the solution obtained is evaporated, whereupon crystallization from ethanol is repeated. Yield: 1.6 g of RGH-4478. Melting point: (after recrystallization from ethanol twice): 180° C. to 182° C. $[\alpha]_D^{25} = +59.25°$ (c=1, chloroform). $R_f = 0.37$ (adsorbent: silica gel; eluting mixture: a 100:5:5:5 mixture of diethyl ether, ethanol, benzene and diethyl amine). Molecular weight: 852.

The $^1$H-NMR spectrum is shown in FIG. 5. From this spectrum the N-methyl singulette characteristics of the starting material is lacking. On the other hand, at 4.48 ppm the multiplette peak of the methylene of the group —N—CH$_2$—O can be seen, while the methyl triplette and methylene quartette of the group O—C$_2$H$_5$ appear at 1.10 and 3.38 ppm, respectively.

The $^{13}$C-NMR spectrum is shown in FIG. 6, while the IR spectrum is attached as FIG. 4.

The characteristic group frequencies of the IR spectrum of the product are as follows:

3470 cm$^{-1}$: OH valence
2970-2830 cm$^{-1}$: OH valence vibrations
1737 and 1230 cm$^{-1}$: acetyl groups
1612 cm$^{-1}$: C=C bond
1595 cm$^{-1}$: aromatic skeleton
742 cm$^{-1}$: 4 A -H next to each other
823 cm$^{-1}$: epoxide ring (b) The 18th to 23rd fractions are combined. The RGH-4478 traces are eliminated by extraction with a 2% sulfuric acid solution, and adjustment of the pH of the acid aqueous phase to 9 with a concentrated aqueous ammonium hydroxide solution. The solution is then extracted with three 0.2 liter portions of chloroform and the chloroform extract is evaporated. Yield: 0.25 g of N-desmethyl-leurosine.

The product obtained, if desired, is converted into N-desmethyl-N-formyl-leurosine by formylation carried out as described in Hungarian Pat. No. 165,986. Yield: 0.24 g of N-desmethyl-N-formyl-leurosine.

(c) The 24th to 28th fractions are combined and evaporated. Yield: 4.42 g of N-desmethyl-N-formyl-leurosine.

EXAMPLE 6

Following the procedure described in Example 2 but starting from 5 g of leurosine sulfate instead of vinblastine sulfate 3.7 g of N-desmethyl-N-formyl-leurosine sulfate are obtained.

EXAMPLE 7

5 g (5.5 mmoles) of vinblastine sulfate dried until alcohol-free are dissolved in 1000 ml of ethanol-free methylene chloride, and to the solution 120 ml of acetic acid and 3.2 ml (10 equivalent) ethanol are added. The solution is cooled to −55° C. and a solution of 2.5 g of chromium trioxide in 470 ml of acetic anhydride cooled to −55° C. is added. The reaction mixture is stirred at −55° C. for 40 to 45 minutes, whereupon the pH is adjusted and the methylene chloride phases are evaporated as described in Example 4. Yield: 4 g of a diindole-alkaloid mixture.

The 4 g mixture product obtained is dissolved in 24 ml of a 8:2 mixture of benzene and chloroform and the solution is passed through a chromatographic column filled with 200 g of alumina, having an activity grade of III. Elution is carried out in the following way:

As an eluant initially 5 to 6 liters of an 8:2 mixture of benzene and chloroform are used, the eluates are combined and evaporated. 2.4 g of crude RGH-4451 are obtained. Recrystallization of the crude product from ethanol affords crystalline RGH-4451, which has the same characteristics as described in Example 1.

Elution is then repeated with 3 to 4 liters of a 1:1 mixture of benzene and chloroform. The combined fractions containing N-desmethyl-vinblastine as well as the fractions containing vincristine are combined and evaporated separately. Yield 0.4 g of N-desmethyl-vinblastine and 0.8 g of vincristine.

EXAMPLE 8

Following the procedure described in Example 7 but carrying out the reaction in the presence of 9.5 ml (30 equivalent) of ethanol, the products of Example 7 are obtained, with the same yields. The physical characteristics of the products are also identical with those described in Example 7.

We claim:

1. A method of treating leukemia, carcinoma, or lymphoma in an animal which comprises the step of administering to said animal a pharmaceutically effective amount of the formula (Ia)

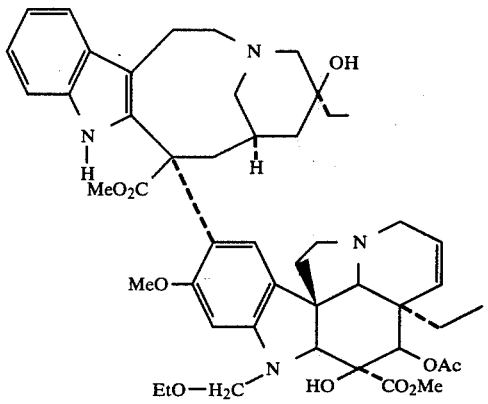

or a pharmaceutically acceptable acid addition salt thereof.

2. A process for the preparation of a compound of the formula (Ia)

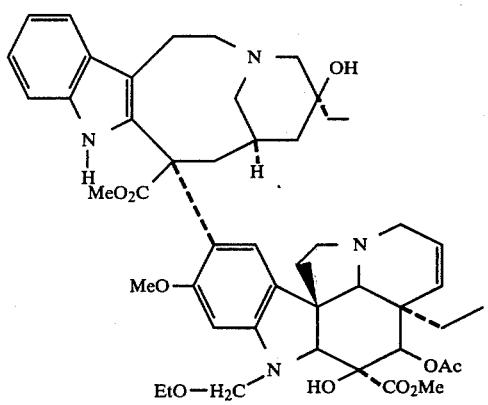

or a pharmaceutically acceptable acid addition salt thereof, which comprises the steps of:
 (a) oxidizing vinblastine or a pharmaceutically acceptable acid addition salt thereof with chromic acid or an alkali metal dichromate at a temperature of −90° C. to −45° C. in the presence of a water-immiscible organic solvent in which alkaloids are readily soluble, acetic anhydride, glacial acetic acid, and ethanol in an amount up to 10% by volume of the water-immiscible organic solvent;
 (b) adjusting the pH of the oxidation reaction of step (a) to a range of 8 to 10 by adding an aqueous alkaline solution thereby forming an organic phase containing alkaloids and an aqueous phase at a temperature no higher than 50° C.;
 (c) separating the aqueous phase from the organic phase to leave an alkaloid mixture and driving the water-immiscible organic solvent therefrom; and
 (d) separating the desired product from the alkaloid mixture leaving behind a residue containing vincristine and N-desmethyl-vinblastine.

3. The process defined in claim 2, step (a), wherein the ethanol is present in an amount between 0.1 to 3% relative to the volume of the water-immiscible organic solvent.

4. The process defined in claim 2, step (a), wherein the water-immiscible organic solvent is chloroform or methylene chloride.

5. The process defined in claim 2, step (b), wherein the aqueous alkaline solution is an aqueous solution of ammonium hydroxide.

6. The process defined in claim 2, step (d), wherein the desired product is separated from the alkaloid product by thin layer chromatography.

7. The process defined in claim 2, further comprising the steps of:
 (e) separating the vincristine from the N-desmethyl-vinblastine; and
 (f) formylating the N-desmethyl-vinblastine to yield additional vincristine.

* * * * *